United States Patent [19]

Perry et al.

[11] 4,041,468
[45] Aug. 9, 1977

[54] METHOD AND SYSTEM FOR ANALYSIS OF AMBULATORY ELECTROCARDIOGRAPHIC TAPE RECORDINGS

[75] Inventors: John H. Perry, Silver Spring, Md.; David S. Salsburg, New London; Colin R. Taylor, Waterford, both of Conn.

[73] Assignee: Pfizer Inc., New York, N.Y.

[21] Appl. No.: 730,628

[22] Filed: Oct. 7, 1976

[51] Int. Cl.² .............................................. G06F 3/12
[52] U.S. Cl. .................................................. 364/900
[58] Field of Search .................. 340/172.5; 445/1; 235/151.3, 151.13

[56] References Cited

U.S. PATENT DOCUMENTS

| 3,473,153 | 10/1969 | Lehnhardt et al. | 340/172.5 |
| 3,557,352 | 1/1971 | Hogg et al. | 235/151.3 |
| 3,665,419 | 5/1972 | Hartmann | 340/172.5 |
| 3,916,370 | 10/1975 | Neeley | 340/172.5 |
| 4,000,461 | 12/1976 | Barber et al. | 235/151.3 X |

OTHER PUBLICATIONS

The Argus/H System for Rapid Analysis of Ventricular Arrhytymias - Biomedical Computer Laboratory and Department of Medicine, Washington University School of Medicine, St. Louis, Missouri 63110 - pp. 37-42.

High Speed Rhythm and Morphological Analysis of Continuous ECG Recordings - Douglas R. Hansmann, Ph. D - Cadio-Dynamics Laboratories, Inc., Beverly Hills, Calif. — pp. 47-54.

Continuous Monitoring of Ambulatory Patients With Coronary Disease - Ramanuja Iyengar et al. - Progress in Cardiovascular Diseases, vol. XIII, No. 4; Jan. 1971 - pp. 392-404.

The Reliability of Intermittent ECG Sampling in Arrhythmia Detection - Lars Ryden, M. D. et al. - Circulation vol. 52, Oct. 1975 - pp. 540-545.

Primary Examiner—Harvey E. Springborn
Attorney, Agent, or Firm—Connolly and Hutz

[57] ABSTRACT

An ambulatory electrocardiographic tape recording (DCG) taken over an extended period of time, such as 24 hours, is analyzed with substantial accuracy by randomly selecting a sample of time periods of a specific duration (such as a 2% sample) and printing out a hard copy record of the electrocardiogram at these times for visual analysis. The simplicity of this method and the system performing it combined with high accuracy in quantifying cardiac arrhythmias makes it perferable for most clinical purposes to conventional methods of analyzing DCG's.

10 Claims, 4 Drawing Figures

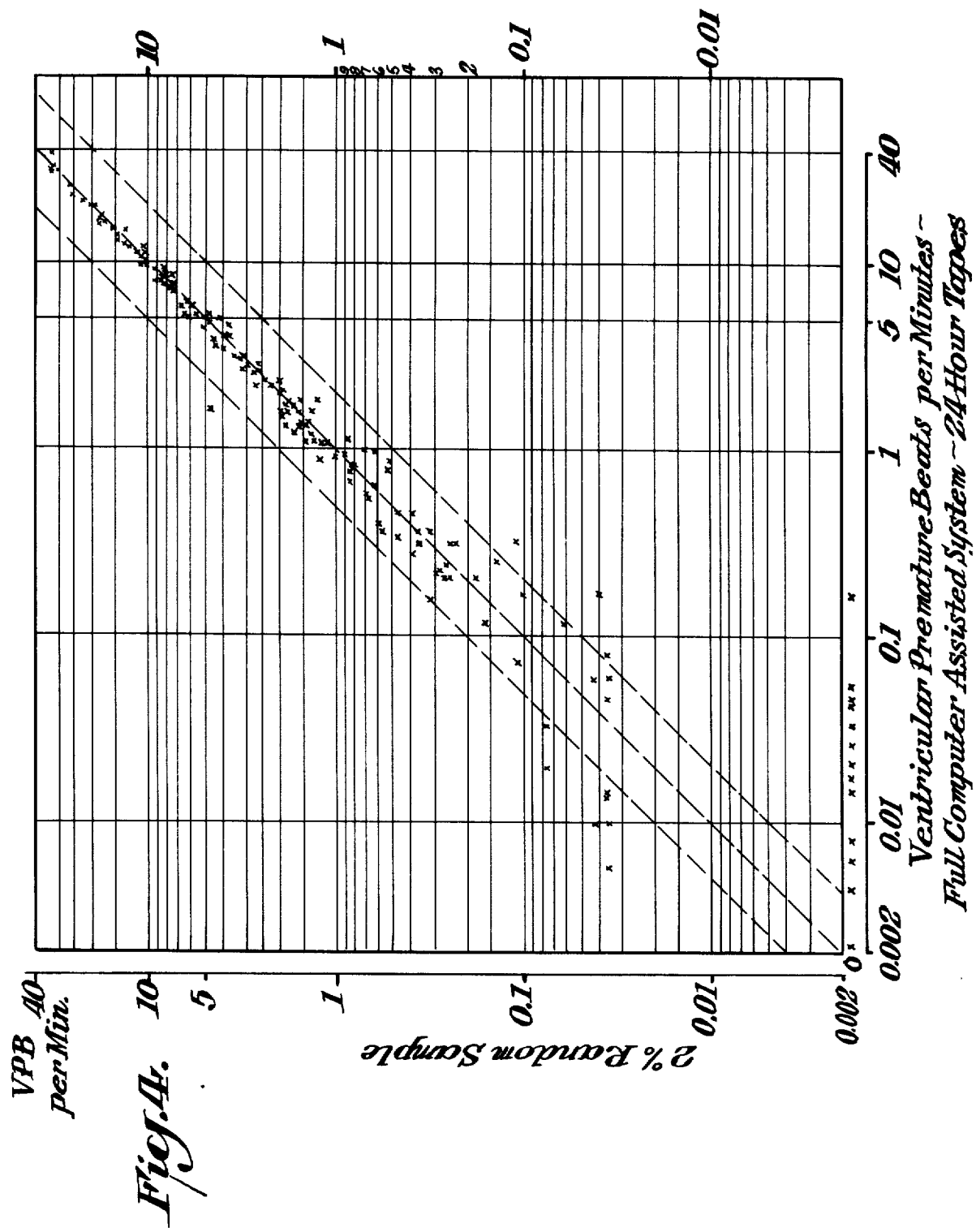

METHOD AND SYSTEM FOR ANALYSIS OF AMBULATORY ELECTROCARDIOGRAPHIC TAPE RECORDINGS

BACKGROUND OF THE INVENTION

This invention relates to a method and system for rapidly and accurately analyzing ambulatory electrocardiographic tape recordings taken over substantial periods of time, such as 24 hours. Heretofore magnetic tape recordings of ambulatory electrocardiograms, such as provided by Holter tapes have been accomplished by various computer assisted techniques. Holter is the trademark of Extracorporeal Medical Specialties Inc., King of Prussia, Pa. for a system of electromagnetic tape recordings of electrocardiograms. Performing computer assisted analysis is extremely laborious and time consuming and in some instances does not provide completely satisfactory results. An object of this invention is to provide a rapid, convenient and time-saving method and system for analyzing magnetic tape electrocardiograms, which provide substantially accurate results.

SUMMARY

In accordance with this invention condensed paper printout of selected electrocardiographic (ECG) segments is generated by (a) analog to digital conversion during rapid tape drive of the ECG signal for the selected ECG segments → storing of the digitized signal → paper printout of the digitized signal, or (b) control of the tape drive of the conventional scanner so that the scanner changes to real time tape drive (i.e. generating the ECG signal at the same rate as it was recorded) followed by either (1) condensed paper printout of the analog signal obtained from the scanner for the required segments or (2) standard rate paper printout of the analog signal using the ECG printout device incorporated in the conventional scanner.

BRIEF DESCRIPTION OF THE DRAWINGS

Novel features and advantages of the present invention will become apparent to one skilled in the art from a reading of the following description in conjunction with the accompanying drawings wherein similar reference characters refer to similar parts and in which.

Figure 2:
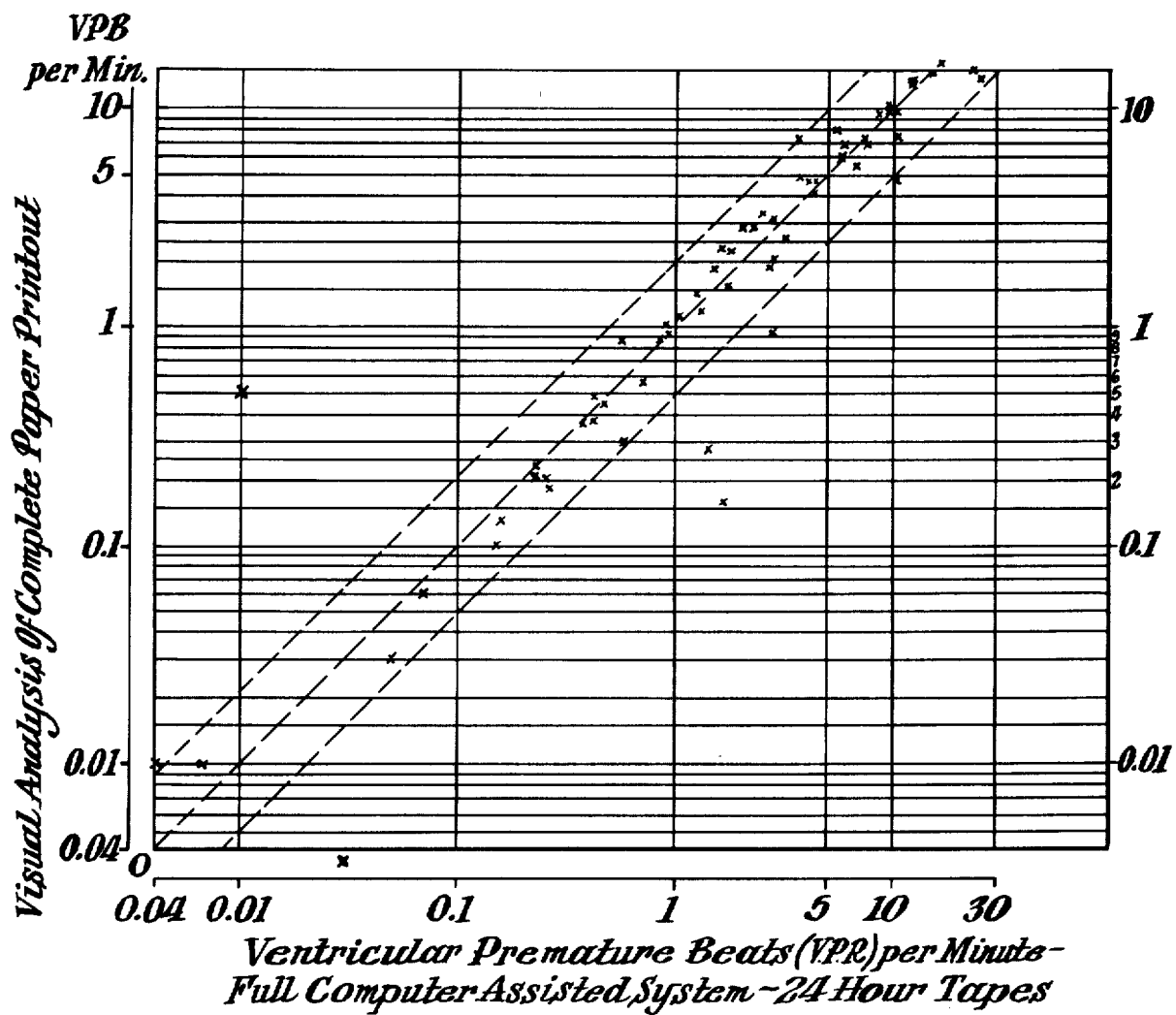
FIG. 2 is a chart comparing the results obtained by the full computer assisted system developed by the present inventors with those obtained by human real time visual analysis of the entire DCG tapes.

FFIG. 3 is a chart comparing the results obtained by conventional DCG scanning with results obtained by the full system the accurate results of which are described in FIG. 2.

FIG. 4 is a chart comparing the results of the full computer system with the results obtained using the invention of this present application.

DESCRIPTION OF THE PREFERRED EMBODIMENT

Figure 1:
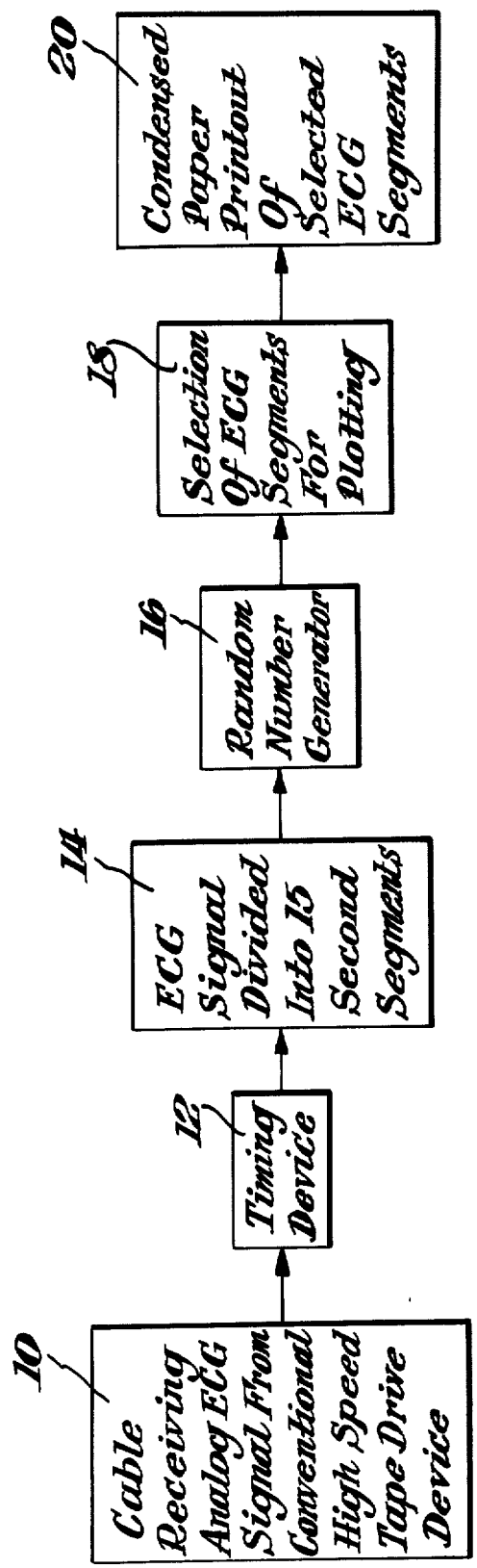
FIG. 1 is a block diagram of a system which is one embodiment of this invention.

FIG. 1 is a block diagram of a system which is one embodiment of this invention. Block 10 represents a cable receiving analog ECG signals from a conventional high speed tape drive device. It feeds the signals to timing device 12, which in turn creates in block 14 an ECG signal divided into segments, for example, of 15 second duration. This input is provided to random number generator 16, which applied a random sample number obtained in a manner later described. Block 18 generates from the input of prior blocks a selection of ECG segments for plotting, which are then printed out as represented by block 20 as a print out of selected ECG segments.

The invention may be used either as an attachment to a conventional commercially available DCG scanner (e.g. Avionics electrocardioscanner) or as a component in an automated or semiautomatic analysis system (such as the computer assisted system developed by the present inventors).

The random sample number is obtained as follows: A seed is taken from the real time clock in the system and is applied as input to the software random number generator which generates an integer number $(x)$ from 1 to 50. The $x^{th}$ member of the first block of fifty 15 second segments is selected.

Similarly, further random members are selected from subsequent 50 segment blocks until an approximately 2% sample has been obtained from the entire tape. Should a greater than 2% sample be required, the procedure is appropriately altered.

Arrhythmia analysis by random sampling of unprocessed ECG data in DCG tapes has not been previously used. Indeed, it has been argued on theoretical grounds that periodic sampling methods would not be useful, Lars Ryden, M.D. Anders Waldenstrom, M.D., and Stig Holmberg, M.D. (1975), Circulation, Volume 52, pages 540–545. The question of whether a random subsample of the tape is sufficiently representative of the entire tape depends upon whether the occurrence of events to be detected is a Poisson process. A crucial theoretical requirement of a Poisson process is that the events occur with constant probability in equal intervals of time no matter where they are taken, across the entire tape. The Ryden, Waldenstrom, and Holmberg paper shows that this assumption does not hold for tapes running several hours. However, if the random sample is selected from a short segment of tape, the events occur with a sufficiently uniform rate that a random sample taken from that short segment will come close to meeting this requirement.

A crucial portion of this invention is, thus, that the tape signal be divided into many short intervals (10–20 minutes each) and one random sample taken from each interval. As a check on the validity of assuming a Poisson process, the counts of observed events per random sample were compared to the expected counts using Chi-Square goodness of fit tests. This was done for various frequencies of single ventricular premature beats (VPB), paired VPB (VP), ventricular tachycardia (VT), rapid and slow supraventricular premature beats (SVPB), paired SVPB (SP) and supraventricular tachycardia (ST). The significance levels of all the Chi-Square tests were greater than 0.20, indicating that all deviations from expected were well within acceptable random error. Use of this invention has been shown to provide results superior in accuracy to those obtained by conventional DCG scanning and at least as accurate at clinically meaningful arrhythmia frequencies as those obtained by a number of complex computer assisted systems or by laborious real time human analysis. The invention provides results more rapidly and more economically than those obtained with complex computer assisted systems.

Figure 3:
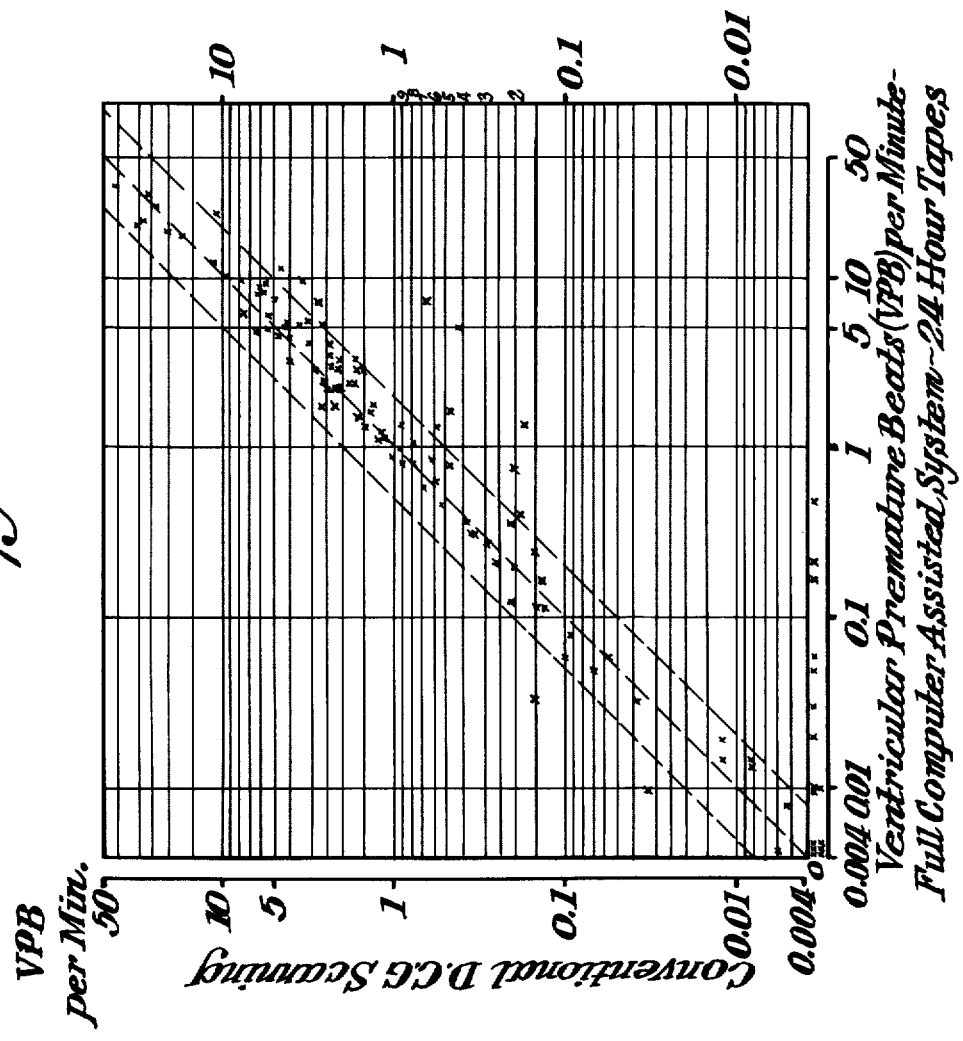

FIG. 2 shows the results obtained with the full, computer assisted system developed by the inventors compared with those obtained by human real time visual analysis of entire DCG tapes. It is clear that an excellent correlation is obtained with the vast majority of tapes. Further review of the disparate results demonstrated that these were related to differences in human diagnostic interpretations. Further validation of the full system was obtained by comparison of results obtained with two semiautomated systems for analysis of DCG tapes. FIG. 3 shows the results obtained by conventional DCG scanning, Iyengar, R., Castellanos Jr., A. and Spence, M. (1971): Prog. Cardiovasc. Dis., 13, 392. versus results with the accurate full system developed by the present inventors described above. It is seen that, although some correlation is noted, many widely divergent results were noted - indicating that conventional DCG analysis is unreliable.

FIG. 4 compares the results of the full computer system together with the results using the invention described in this application. It is clear that the correlation is excellent at clinically meaningful arrhythmia rates; accuracy is less at ventricular premature beat rates of <0.1/minute but it is generally accepted that only much higher arrhythmia rates (e.g. 5/minute according to many workers) are medically significant.

Accordingly it is submitted that the invention:

1. Is a new procedure
2. Has been shown to be clinically reliable in analysis of cardiac arrhythmias in DCG tapes.
3. That the results obtained are superior to those obtained with conventional procedures for analysis of DCG tapes.
4. That the method provides results equivalent in quality to those obtained with complex computer assisted systems but is much quicker and more economical.

The following describes the different full computer systems previously used for analyzing magnetic DCG tapes. The first description is of the inventors full computer system herein described as the P.I. system. The P.I. system for Holter analysis was developed since no adequate commercial or developmental system was found after review of available systems. The P.I. approach was based on the following considerations:

1. Specific computer diagnosis of cardiac arrhythmias is rudimentary in all systems developed to date. Accordingly definitive arrhythmia diagnosis was based on visual scanning of the raw ECG signal by trained personnel after initial computer processing.
2. Since cardiac arrhythmias are usually associated with abnormalities of cardiac rhythm, it was decided on clinical grounds to use abnormality of the time interval between beats (RR interval) as a method whereby the computer could divide the heart beats in the DCG tape into "normal" and "abnormal" types — with the expectation that the vast majority of cardiac arrhythmias would be present in the abnormal category. A powerful algorithm was developed for this purpose and proved extremely successful. Individual RR intervals are allocated to the abnormal category if their values lie outside a statistically derived index of normal variation compared with an exponentially weighted running average of normal RR intervals. The index of normal variation is based on the statistical properties of the normal RR intervals in the immediately preceding time period and thus is individualized for that patient at that moment in time.
3. On clinical grounds, abnormal RR intervals were divided into various catatories of rhythm patterns each of which tends to be associated with a different type of cardiac arrhythmia (FIG. 5). Computer programs to detect each pattern (or "signature") allow categorization of abnormal beats by signature type.
4. Computer plotting of appropriate samples of raw ECG signals from each computer category allows definitive arrhythmia diagnosis by visual scanning. The errors involved in the sampling procedure have been estimated.

II. Categorization by Computer

Abnormal RR interval patterns are divided into various categories (signature types) which may be expected on clinical grounds to be associated with specific arrhythmia types:

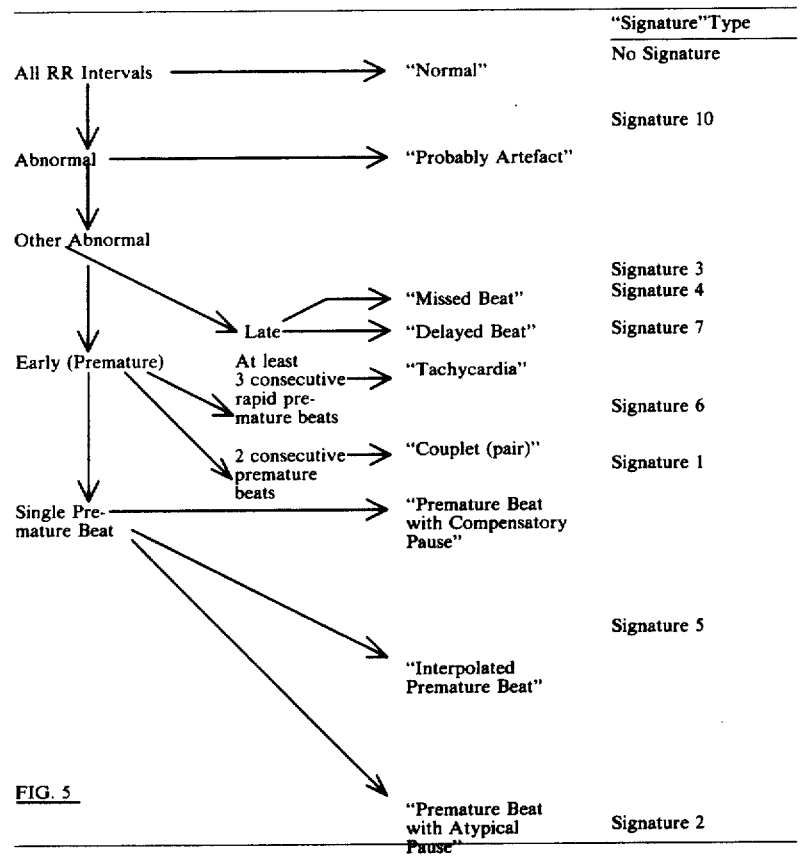

FIG. 5

In addition signatures are allocated to episodes with an RR interval pattern consistent with Bigeminy (signature 8) or Trigeminy (signature 9).

In 24-hour tapes, abnormal beats in signatures 1—7 are also grouped in blocks of four hours (8 a.m. -11.59 mid-day; 12-3.56 p.m.; 4p.m. -7.59 p.m.; 8 p.m. -11.59 p.m.; 12 -3.59 a.m.; 4 a.m. -7.59 a.m.) and within each four hour block are also grouped into "active" and "inactive" types according to whether the underlying normal heart rate at the time is above or below the median heart rate for the 4-hour period. Thus, there are 85 possible categories of abnormal RR intervals -7 (signature 1-7) × 6 (4-hour blocks) × 2 (active/inactive) + (signature 10). This provides a highly stratified sample for each 24-hour tape.

ECG samples selected for visual scanning are obtained as follows: If the number of episodes in all signature types combined is not more than approximately 1,200, all abnormal episodes are plotted. If the total number of episodes is more than 1,200, an approximately 1,200 episode random stratified sample is obtained from the 85 categories. Categories containing fewer episodes have higher sampling rates. Plotting of the ECG is at the standard rate of one inch/second.

Reproduction of the ECG signal for visual analysis is obtained from a digitized record of the entire tape.

A 2% random sample of the tape in blocks of 15 seconds (at a rate of 0.5 inches/second) is also plotted with signature numbers being printed immediately below beats determined by the computer to have abnormal RR intervals. Visual analysis of the random sample allows estimation of the false negative rate and permits independent verification of the results from the signature plots.

Following ectopic beat detection, another program selects samples of the data to be plotted. The program first scans the signature file, counting the number of events in each category (signature/period/activity). For signatures 6 and 7, a run of consecutive ectopics with the same signature is considered to be an event. For other signatures, each ectopic is an event. Signatures 1 through 5 are sampled proportionately with a lower limit of 10 samples of all the events, whichever is smaller, in any category. The proportion used in sampling is chosen dynamically to make the total number of samples approximately 900. Signatures 6 and 7 are sampled in the same way, with the proportion chosen to make the total number of samples approximately 200.

This program also searches for sequences of ectopics which define bigeminy and trigeminy. These sequences are designated signatures 8 and 9 respectively. A sample of 25 or all events, whichever is smaller, is taken from each of the signatures 8 and 9.

All sampling in the DCG system is done using the same algorithm. If M samples are to be taken from a population of size N, random integers in the range 1 to N are generated until there are M different integers. The initial seed for the random number generator is taken from the computer system's clock, assuring a different starting point each time.

Following the selection of ectopics for plotting, a program selects 60 or all artefact regions, whichever is smaller. Another program selects a random 2% sample of the raw data, without regard to ectopic beats.

All samples for plotting are passed to the plot programs as files containing the intervals in time which are to be plotted. These files are called plot index files. The three plot programs are slight ariations on the same algorithm.

Certain data from the system are retained in analyzed form on computer magnetic tape for later use. These include a summary file containing the results of calculations, statistics, and counts of ectopics with sample sizes, the RR file, and the signature file. In addition, although the A/D file is too large to save economically, that A/D data which was plotted, as identified by the plot index files, is encoded and saved on tape. The original analog tape is also retained.

The following is a comparison with results from a commercial analysis system (Cardiodynamics Laboratories) and a Computer Assisted Research system (Washington University, St. Louis). Cardiodynamics Laboratories (Los Angeles) provides a Holter tape analysis giving quantitative measurement of premature beats (supraventricular and ventricular) and qualitative analysis of other arrhythmias. Measurement of premature beats is obtained by RR interval based computer generated detection of abnormal beats followed by visual inspection of samples of these abnormal beats for precise diagnosis ("High speed Rhythm and Morphological Analysis of Continuous ECG Recordings," Hansmann, D.R. "Computers in Cardiology" (1974); pages 47-54; IEEE catalog no. 74CH0879-7C; IEEE Computer Society, Long Beach, Cal.

The Biomedical Computer laboratory and Department of Medicine at the Washington University School of Medicine, St. Louis, Missouri have developed a computer assisted system for Holter tape analysis which involves visual analysis of "abnormal beats" characterized by computer detected abnormality of QRS configuration ("The Argus/H System for Rapid Analysis of Ventricular Arrhythmias" Nolle, F. M. et al, (1974), pages 37-42, IEEE catalogue no. 74CH0879-7C).

Some of the similarities and differences between the three computer assisted systems are provided in the following Table 1.

TABLE 1

|  | Present Inventors' Full Computer System | Cardio- dy- namics | Argus/ H |
| --- | --- | --- | --- |
| Quantitative Analysis of |  |  |  |
| Single VPB | Yes | No | Yes |
| Single SVPB | Yes | No | No |
| SVPB Couplets (Pairs) | Yes | No | No |
| VPB Couplets | Yes | No | Yes |
| ST | Yes | No | No |
| VT | Yes | No | Yes |
| Bigeminy | Yes | No | No |
| Trigeminy | Yes | No | No |
| AV Dissociation | Yes | No | No |
| Total SVPB (Single+Couplets +Runs) | Yes | Yes | No |
| Total VPB (Single+Couplets +Runs | Yes | Yes | Yes |
| Detects Arrhythmias where R Wave Detector Inaccurate Estimates False Negative Rate and Corrects | Yes | No | No |
| Total Counts Accordingly | Yes | No | No |
| Provides Counts of Individual VPB Morphologies | Yes | Yes | No |
| Provides Independent Check of Counts by Random Sample | Yes | No | No |
| Provides Confidence |  |  |  |

TABLE 1-continued

|  | Present Inventors' Full Computer System | Cardio- dy- namics | Argus/ H |
| --- | --- | --- | --- |
| Bounds on Degree of Accuracy of Each Count | Yes | No | No |

III. COMPUTER METHODS USED IN DCG TAPE ANALYSIS

The present computer system for ECG analysis consists of an Avionics 660 electrocardioscanner tied to a DEC PDP-11/10 computer which communicates with a Decsystem-10 computer.

The 660 sends the PDP-11 two signals: an analog ECG voltage and a scope trigger pulse which occurs whenever the 660 detects an R wave. The trigger pulse is detected by a Schmidt trigger in the PDP-11. The analog ECG signal is converted to a 12-bit digital value by an analog-to-digital converter in the PDP-11. The analog tape is played back on the 660 at 60 times real time. A/D conversions are performed by the PDP-11 in response to a 6000 Hz clock signal, giving a temporal resolution of 100 points per tape second. The least significant bit of the A/D conversion is less than the step size of our plotter, so the voltage resolution is limited solely by the plotter.

Each A/D conversion, together with a bit indicating whether the trigger pulse was detected during the interval between the current and the previous A/D conversion, is transmitted to the Decsystem-10, where it is written onto a disk. The entire 24-hour tape is transmitted, yielding a file containing approximately 8,640,000 A/D conversions residing on the Decsystem-10.

The remainder of the processing is performed by the Decsystem-10. First, a program reads the A/D file, counting A/D conversions between trigger pulse bits, to get the RR intervals, which are written on the disk, creating the RR file. The RR file is then read by a program which looks for RR intervals in two categories: intervals longer than 3 seconds, and strings of two or more intervals less then 0.3 seconds. Signal intervals longer than 0.3 seconds may be embedded with the latter category, as long as two or more short intervals begin the string. Experience has shown that these portions of the tape are artefact. These events are written into an artefact file on the disk. All subsequent programs ingore those parts of the RR file which are classified as artefact.

Following artefact detection, a program calculates the median RR interval in each 4-hour period. Periods are numbered from 1 through 12, starting at 12:01 a.m. of the day the tape is started and ending at midnight of the day the tape ends. The median RR intervals are used by the ectopic beat detection program as one of the classifications for ectopic beats.

The ectopic beat detection program begins by estimating the average normal RR interval and a window of variability for the beginning of the tape. The mean RR interval is calculated for each of 30 groups of 30 RR intervals, starting on the second beat of the tape. The mean of the first group is taken as an initial estimate of the normal. A regression line is fitted to the 30 means, and the variance about the line is alculated. The ratio of the square root of variance to the mean of the first group is defined as the window W. The procedure outlined above has the advantage of being insensitive to VPB's in the initial groups. The final results of the program are insensitive to the exact value of the initial estimate of the normal RR over a range of $+/-2.5*W*$ RRBAR. The true positive ectopic beats detected are insensitive to the window calculation over a $+/-50\%$ range. The ectopic beat detection proceeds as follows.

Starting with the second RR interval on the tape, each is compared with the moving average normal RR interval. A normal range is defined by:

$$RRBAR(1-2.5*W) < RR < RRBAR(1+5.0*W)$$

If the beat lies within this range, it is considered to be normal. Normal beats are included in the moving average normal RR according to the formula:

$$RRBAR = (1\text{-}EXP(-0.1))\ RR\ +\ (EXP(-0.1))\ RRBAR$$

RR intervals lying outside the normal range are assigned to various categories, called signatures, depending on the pattern of RR intervals.

If the RR interval is larger than the upper limit of the normal range, it is tested for being approximately twice RRBAR. Intervals within the range $$2*RRBAR\ -2.5*W*\ RRBAR\ <\ RR\ <2*RRBAR\ +\ 5.0*W*\ RRBAR$$

are called signature 3 (missed beat), the rest are called signature 4 (delayed beat). Typically, these signatures are ventricular ectopics on which the 660's R wave detector failed.

If the RR interval is smaller than the lower limit of the normal range, the next RR interval, RR2, is examined. If RR2 is greater than the upper limit of the normal range and $$RRBAR(1-2.5*W) < (RR + RR2)/2\ RRBAR(1+5.0*W),$$

the original RR interval is called signature 1 (premature beat with compensatory pause). If RR2 is greater than the lower limit of the normal range but does not fall in the range for signature 1, the original RR interval is called signature 2 (premature beat with atypical pause).

If RR2 is less than the lower limit of the normal range, the next RR interval, RR3, is examined. If RR3 lies in the normal range and (RR+RR2) also lies in the normal range, RR is called signature 5 (interpolated beat). If RR3 is greater than the lower limit of the normal range but the conditions for signature 5 are not satisfied, RR and RR2 are both called signature 6 (pair of premature beats). If RR3 is less than the lower limit of the normal range, RR, RR2, RR3, and all successive beats are called signature 7 (tachycardia) until an interval occurs which is greater than the lower limit of the normal range.

The ectopic beat detection program writes a disk file, called the signature file, which contains information about each ectopic detected. Ectopic beats are classified according to signature type, 4-hour period number, and whether the moving average normal RR interval was above or below the median for the period in which the ectopic occured. If the moving average RR interval was above the median, the beat is called inactive, otherwise it is called active.

24 hour DCG Tapes with significant cardiac arrhythmias of various types (as determined by conventional scanning analysis) were selected from five patients and were processed by each of the three computer assisted systems. Results were as follows for all 4 methods (3 computer assisted methods; one conventional scanning).

a. VPB Rates - VPB rates were reasonably comparable with the four systems. In three of the 5 patients (with VPB rates over 15 per minute) the Argus/H system was unable to provide visually edited results in view of the technician time required for visual review of all computer detected abnormalities. Since the Cardiodynamics system gives a total count of all ectopic beats (whether occurring singly, in couplets or in runs), it does not provide an accurate count of single ectopic beats where frequent couplets and runs are present.

b. VPB Couplet Rates - Investigator scanning appeared accurate only in the single patient with a very high couplet rate. The Argus/H system in the single patient processed gave a result comparable to the present inventors3 system result. Cardiodynamics did not provide quantitative assessment of VPB couplets.

c. Ventricular Tachycardia - Only 2 patients had ventricular tachycardia-detected by Investigator, Cardiodynamics and P.I. system and Argus/H system in the other case.

d. SVPB Rates - The Investigator evaluation did not appear reliable in estimating low SVPB rates in the presence of a high degree of ventricular ectopic activity. The P.I. and Cardiodynamics results were comparable in two cases (08-018-2 and 10-001-1); in two cases, (02-025-3 and 08-017-2) the occurrence of supraventricular tachycardia/transientatrial fibrillation provided a very high "SVPB" rate from Cardiodynamics since this method counted all supraventricular tachyarrhythmia beats and SVPB; in patient 02-023-3 Cardiodynamics called runs of premature beats with ventricular aberration "supraventricular tachycardias" whereas P.I. and Argus/H called these "ventricular tachycardias" — consequently the Cardiodynamics SVPB rate (single + couplets + runs) was higher.

e. SVPB Couplets, Supraventricular Tachycardia and Transient Atrial Fibrillation — the Investigator and the P.I. system provided counts of these arrhythmias while Cardiodynamics noted their presence but not their frequency. In 3 patients transient supraventricular tachycardias/atrial fibrillation were detected (in 2 case by all 3 systems; in one case by P.I. and Cardiodynamics only). There was some disagreement between the human editors as to which events were called "supraventricular tachycardia" or "atrial fibrillation."

In conclusion, all 4 analysis methods provide fairly reliable results when counting frequent single premature beats in the absence of repetitive ectopic activity (although the Argus/H system can not easily analyze tapes with very frequent ectopics). Conventional scanning analysis is not reliable for repetitive ectopic activity and Argus/H does not analyse supraventricular arrhythmias. Only the P.I. system provides quantitative estimates of all arrhythmia types.

TABLE 3

| Patient | SVPB Couplets** (per hour) | | | Supraventricular** Tachycardia (episodes per hr.) | | | Transient Atrial** Fibrillation (episodes per hr.) | | |
|---------|------|------|------|------|------|------|------|------|------|
|         | Inv. | P.I. | Card.| Inv. | P.I. | Card.| Inv. | P.I. | Card.|
| 02-023-3| 0    | 0    | NO   | 0    | 0    | ***  | 0    | 0    | NO   |

TABLE 3-continued

| Patient | SVPB Couplets** (per hour) | | | Supraventricular** Tachycardia (episodes per hr.) | | | Transient Atrial** Fibrillation (episodes per hr.) | | |
|---|---|---|---|---|---|---|---|---|---|
| | Inv. | P.I. | Card. | Inv. | P.I. | Card. | Inv. | P.I. | Card. |
| 02-025-3 | 0 | 0.18 | YES | 6.58 | 7.02 | YES | 0 | 0 | NO |
| 08-017-2 | 0 | 0.39 | YES | 0.04 | 0 | YES | 0.20 | 6.0 | NO |
| 08-018-2 | 0 | 0.19 | YES | 0 | 0.50 | YES | 0 | 0 | NO |
| 10-001-1 | 0 | 0 | NO | 0 | 0 | NO | 0 | 0 | NO |

Inv. = Investigator
P.I. = Present Inventors' System
Arg. = Argus/H system
** = Quantitative Analysis not Provided by Cardiodynamics No Supraventricular Arrhythmia Analysis Provided by Argus/H System
*** = Tachyarrhythmia reported as Supraventricular Tachycardia but "Ventricular Origin Can Not Be Excluded".

TABLE 2

| Patient | VPB (per minute) | | | | VPB Couplets (per hour) | | | |
|---|---|---|---|---|---|---|---|---|
| | Inv. | P.I. | Card. | Arg. | Inv. | P.I. | Card | Arg. |
| 02-023-3 | 2.38 | 5.50 | 4.57 | 5.10 | 0 | 9.42 | YES | 6.92 |
| 02-025-3 | 0 | 0 | 0 | 0.006 | 0 | 0 | NO | 0.04 |
| 08-017-2 | 22.7 | 17.0 | 22.9 | NP | 128 | 120 | YES | NP |
| 08-018-2 | 32.2 | 31.22 | 33.7 | NP | 0.42 | 0.29 | YES | NP |
| 10-001-1 | 14.6 | 17.0 | 16.8 | NP | 0 | 0.05 | YES | NP |

| Patient | Ventricular Tachycardia (per hour) | | | | SVPB (per minute) | | | |
|---|---|---|---|---|---|---|---|---|
| | Inv. | P.I. | Card | Arg. | Inv. | P.I. | Card. | Arg. |
| 02-023-3 | 0 | 0.60 | NO | 0.29 | 0 | 0.05 | 1.12 | NP |
| 02-025-3 | 0 | 0 | NO | 0 | 0 | 0.04 | 3.40 | NP |
| 08-017-2 | 0.08 | 3.60 | YES | NP | 0.17 | 0.32 | 18.0 | NP |
| 08-018-2 | 0 | 0 | NO | NP | 0.17 | 0.002 | 0.02 | NP |
| 10-001-1 | 0 | 0 | NO | NP | 0 | 0 | 0.01 | NP |

(Inv. = Investigator)
(P.I. = Present Inventors' System)
(Card. = Cardiodynamics Inc. System)
(Arg. = Argus/H System)
NP = Analysis Not Provided by Processing System
NO = Arrhythmia Not Noted;
YES = Arrhythmia Noted.
* = Cardiodynamics VPB and SVPB counts are total of single, coupled and tachyarrhythmic beats

We claim:

1. A method for rapidly analyzing an electrocardiographic tape recording comprising the steps of generating and receiving an analog ECG signal from a tape reading device, applying a timing signal to the analog ECG signal to provide an ECG signal divided into segments of predetermined relatively short duration of time, selecting a random number of predetermined time segments constituting a relatively small percentage of the tape recording and plotting the selected segments for visual analysis.

2. A method as set forth in claim 1 wherein approximately a 2-5% sample of the entire tape is selected for plotting.

3. A method as set forth in claim 1 wherein approximately a 2% sample of the entire tape is selected for plotting.

4. A method as set forth in claim 1 wherein the segments are of approximately less than one minute duration.

5. A method as set forth in claim 1 wherein the segments are of approximately a fifteen 2nd duration.

6. A system for rapidly analyzing an electrocardiographic tape recording comprising means for generating and receiving an analog ECG signal from a tape reading device, means for applying a timing signal to the analog ECG signal to provide an ECG signal divided into segments of predetermined relatively short duration of time, means for selecting a random number of predetermined time segments constituting a relatively small percentage of the tape recording, and means for plotting the selected segments for visual analysis.

7. A method as set forth in claim 6 wherein the selecting means is constructed and arranged to plot approximately a 2-5% sample of the entire tape recording.

8. A system as set forth in claim 6 wherein the selecting means is constructed and arranged to plot approximately a 2% sample of the entire tape recording.

9. A system as set forth in claim 6 wherein the means for applying a timing signal is constructed and arranged to provide time segments of less than one minute duration.

10. A system as set forth in claim 6 wherein the means for applying a timing singal is constructed and arranged to provide time segments of about fifteen second duration.

* * * * *